US007883691B2

(12) United States Patent
Kalejman

(10) Patent No.: US 7,883,691 B2
(45) Date of Patent: Feb. 8, 2011

(54) COSMETIC COMPOSITION COMPRISING CAMEL MILK OR COMPONENTS THEREOF

(75) Inventor: Hector Kalejman, Beer Sheva (IL)

(73) Assignee: Lev-Bar Ltd., D.N. Hanegev, IL (US)

( * ) Notice: Subject to any disclaimer, the term of this patent is extended or adjusted under 35 U.S.C. 154(b) by 747 days.

(21) Appl. No.: 10/570,814

(22) PCT Filed: Sep. 6, 2004

(86) PCT No.: PCT/IL2004/000802

§ 371 (c)(1),
(2), (4) Date: Sep. 8, 2006

(87) PCT Pub. No.: WO2005/023208

PCT Pub. Date: Mar. 17, 2005

(65) Prior Publication Data

US 2007/0154443 A1    Jul. 5, 2007

(30) Foreign Application Priority Data

Sep. 8, 2003  (IL) .................................... 157814

(51) Int. Cl.
*A61K 8/97* (2006.01)
*A61K 35/20* (2006.01)
(52) U.S. Cl. ......................... 424/74; 424/535
(58) Field of Classification Search ........................ None
See application file for complete search history.

(56) References Cited

U.S. PATENT DOCUMENTS

| 5,053,219 A | 10/1991 | Giddey et al. |
| 5,447,961 A | 9/1995 | Kim et al. |
| 5,512,278 A * | 4/1996 | Mundschenk ............ 424/78.06 |
| 5,547,602 A | 8/1996 | Schuler |
| 5,576,027 A | 11/1996 | Friedman et al. |
| 2003/0108617 A1 * | 6/2003 | Leithe et al. ................. 424/535 |

FOREIGN PATENT DOCUMENTS

| EP | 0 577 052 A | 1/1994 |
| WO | WO 02/05828 | 1/2002 |

OTHER PUBLICATIONS

Wernery et al. (Milchwissenschaft. 2003; 58 (5-6): 277-279).*
Farah (Journal of Dairy Research. 1993; 60 (4): 603-26).*
Restani, Gaiaschi, Plebani, Beretta, Cavagni, Fiocchi, Poiedi, Velona, Ugazio & Galli, Cross-reactivity between milk protein from different animal species, Clinical & Experimental Allergy, Jul. 1999, p. 997, V.29, Issue 7.
International Search Report PCT/IL2004/000802.
International Preliminary Report on Patentability PCT/IL2004/000802.
Written Opinion published Mar. 8, 2006 for PCT/IL04/23208.

* cited by examiner

*Primary Examiner*—Shanon A Foley
(74) *Attorney, Agent, or Firm*—Martin Fleit; Paul D. Bianco; Fleit Gibbons Gutman Bongini & Bianco PL

(57) ABSTRACT

The present invention provides cosmetic compositions and products that contain camel milk or components thereof, wherein the milk or components may be pre-treated by a physical or biochemical process. The invention further relates to a process for preparing cosmetic compositions containing camel milk or components thereof.

16 Claims, No Drawings

COSMETIC COMPOSITION COMPRISING CAMEL MILK OR COMPONENTS THEREOF

FIELD OF THE INVENTION

The present invention relates to cosmetic compositions and products that contain camel milk or components thereof, as well as to a process for their preparation.

BACKGROUND OF THE INVENTION

Animal milk has been a rich source of nutrients since the dawn of human history. Providing not only energy, but also amino acids, important elements and protecting factors, milk has been used in the preparation of pharmaceutical and cosmetic compositions. Beside calcium, magnesium, and phosphorus, milk contains additional potentially benign components, of which vitamins soluble in fats and protein factors are of special interest for cosmetic compositions, among said protein factors being, for example, growth factors and lactoferrin. WO 02/05828 relates to a composition for treating or preventing skin damage, comprising growth factors derived from milk.

Milk of ruminants, and predominantly bovine milk, has been utilized most. Among drawbacks of cow milk is a widespread allergy to it, afflicting in various of its forms as much as 50% individuals in some populations. Another problem with cow milk may be antibiotic toxicity in dairy products.

It is an object of this invention to provide a cosmetic composition comprising milk or a component thereof which keeps all the benign properties of milk but is free of the drawbacks related to cow milk. Camel milk has been traditionally used by certain ethnic groups, and it was found that, in some respects, its composition is closer to the human milk than cow milk. It was shown that IgEs from children allergic to cow milk were capable of recognizing proteins from mammals bred in European countries, but not from the camel [Restani et al.: Clinical & Experimental Allergy 29 (1999) 997-1004]. It is therefore another object of this invention to provide a cosmetic composition comprising camel milk or a component thereof.

Other objects and advantages of present invention will appear as description proceeds.

SUMMARY OF THE INVENTION

The present invention provides a cosmetic composition comprising camel milk or at least one cosmetically effective component of camel milk as an active ingredient wherein said camel milk or said component may be treated by a physical process that comprises techniques such as, for example, evaporation, lyophylization, precipitation, filtration, extraction, heat treatment, and centrifugation. Said camel milk or a component thereof may be further treated by a biochemical process that comprises techniques such as, for example, enzymatic treatment, microbial treatment, and chromatography. A composition according to this invention comprises camel milk or a component thereof preferably in a concentration of from 1.5 to 30% w/w, a lipid component preferably in a concentration of from 3 to 65% w/w, a polyalcohol component preferably in a concentration of from 0 to 15% w/w, and it may further comprise vitamin A, vitamin E, surfactant, stabilizer, antiseptic, vegetal tincture, antioxidant, and components adjusting visual, olfactory, and consistency properties. Said lipid component is preferably selected from fatty ester, fatty alcohol, wax, petrolatum, fatty acid or its salt, and their mixture. Said polyalcohol is preferably selected from glycerol, propylene glycol, sorbitol, polyethylene glycol, and saccharide. The ratio of components can be adjusted according to the intended application of the cosmetic composition.

The invention further provides cosmetic products comprising camel milk or a component thereof, wherein said milk or component may be processed by a physical, chemical, or biological treatment. The product of this invention is preferably shaving cream, hand cream, shampoo, soap, conditioner, body cream, sun skin-protection, face cream, or body lotion.

This invention also relates to a process for the preparation of a cosmetic composition, comprising providing camel milk or a component thereof; optionally treating said milk or said milk component; and mixing said milk or a component thereof with a lipid component, water, and at least another constituent selected from the group consisting of polyalcohol, surfactant, component adjusting visual properties, component adjusting olfactory properties, component adjusting consistency, vitamin A, vitamin E, and antiseptic, wherein said components are mixed in any order until homogeneity. A process according to this invention may comprise treating said milk or a component thereof by physical or biochemical techniques, such as, for example, evaporation, lyophylization, precipitation, filtration, extraction, heat treatment, centrifugation, chromatography, enzymatic treatment, and microbial treatment. In a preferred embodiment, camel milk or its component is heat-treated before mixing with other components.

DETAILED DESCRIPTION OF THE INVENTION

Beside providing nutrition and elements, milk has been shown to comprise cell stimulatory and anti-microbial factors. The former are related to cytokines present in milk, and the latter to, among others, protein lactoferrin which is also supposed to have anticancer effects and to enhance immunity. Another milk protein, major whey protein β-lactoglobulin, has binding sites for minerals and vitamins A and E. The mentioned features make milk a desirable component in cosmetic products. In addition to being a weaker allergen, camel milk has been found to be more similar to human milk than bovine milk in several parameters, namely in concentrations of fats and casein. Camel milk further contains more lactoferrin than cow milk.

It has now been shown that the desirable properties of milk can be utilized in cosmetic compositions by comprising camel milk or a component thereof.

The composition of this invention comprises camel milk or a component thereof, preferably in a concentration of from 1.5 to 30% w/w, a lipid component preferably in a concentration of from 3 to 65% w/w, optionally a polyalcohol component in a concentration of from 0 to 15% w/w, and may further comprise vitamin A, vitamin E, other vitamins, surfactant, antiseptic, preservative, stabilizer, and components adjusting visual, olfactory, and consistency properties. Said lipid component is preferably selected from fatty ester, fatty alcohol, wax, petrolatum, fatty acid or its salt, and their mixture. Said polyalcohol is preferably selected from glycerol, propylene glycol, sorbitol, polyethylene glycol, and saccharide.

The cosmetic composition of this invention may comprise a component of camel milk, wherein said component can be obtained from the whole milk by a physicochemical or biochemical process that comprises one or more techniques selected from evaporation, lyophylization, precipitation, filtration, extraction, heat treatment, centrifugation, etc. In one embodiment, said component is a fat fraction of milk, obtained by centrifugation. Said camel milk or a component thereof may be further treated by a process that may comprise techniques mentioned above.

This invention is directed to cosmetic products, such as shaving cream, hand cream, shampoo, soap, conditioner, body cream, sun skin-protection, face cream, or body lotion. The ratio of components in the cosmetic composition according to this invention can be adjusted according to the intended application of the cosmetic composition. In a preferred embodiment of this invention, the cosmetic composition is a body cream containing about 20% camel milk. In another preferred embodiment of this invention, the cosmetic composition is a liquid soap containing 1.5 to 3% of fat fraction of camel milk.

The present invention further relates to a process for the preparation of a cosmetic composition, comprising providing camel milk or a component thereof; optionally treating said milk or said milk component; and mixing said milk or a component thereof with a lipid component, water, and at least one other constituent selected from the group consisting of polyalcohol, surfactant, component adjusting visual properties, component adjusting olfactory properties, component adjusting consistency, vitamin A, vitamin E, and antiseptic, wherein said components are mixed in any order until homogeneity. Any techniques known in the art of cosmetics may be used for preparing compositions and homogenizing them. Said component can be obtained from the whole milk by a physicochemical or biochemical process that comprises one or more techniques selected from evaporation, lyophylization, precipitation, filtration, extraction, heat treatment, centrifugation, etc. The same techniques may be used for processing the whole milk before using it in the preparation of the cosmetic composition of this invention. In one embodiment, said component is a fat fraction of milk, obtained by centrifugation. In a preferred embodiment of this invention, a cosmetic composition comprises camel milk, which is heat-treated before introducing into the composition. This treatment may comprise a temperature between about 65° C. and 72° C., and may be performed, for example, for about 15 minutes.

The invention will be further described and illustrated in the following examples.

EXAMPLES

Materials and Methods

Camel milk was obtained by milking camels of species *Camelus dromedarius*. Milk was heated at 72° C. for 15 minutes. Usually, milk containing at least 3% fat, and 2% proteins was used.

The fat fraction of camel milk was prepared by centrifuging milk after the above described heat-treatment.

Components for cosmetic compositions were separately heated to 75° C. before mixing, and the milk or milk component was mixed with other components at room temperature.

The contents are given in weight percents (%).

BHT stands for butylhydroxy toluene, BHA stands for butylhydroxy anisole, se stands for self emulsion, dm stands for dimethyl.

Example 1

Calendula cream with camel milk was prepared by mixing:

| | |
|---|---|
| Camel milk | 20% |
| Stearic alcohol | 25% |
| Vaseline | 25% |
| Propylene glycol | 2% |
| Sodium lauryl sulfate | 3% |
| Calendula tincture | 5% |
| Nipagin | 0.1% |
| Nipasol | 0.1% |
| Perfume natural | 0.1% |
| Water to | 100% |

Calendula is an antiseptic, it improves blood flow to the effected area; has benign effect on acne and diaper rash; and being antifungal, it can be used in treating athlete's foot, ringworm, and *Candida*; and it also supports healing, when applied to cold sores.

Example 2

Shaving cream was prepared by mixing:

| | |
|---|---|
| Camel milk | 3% |
| Stearic acid | 18% |
| Glycerol | 5% |
| Triethanolamine | 2% |
| Lanolin | 3% |
| Paraffin | 3% |
| Borax | 2% |
| Water to | 100% |

White and smooth cream was obtained, providing agreeable sensation, to be used with or without brush.

Example 3

Hand cream with camel milk was prepared by mixing:

| | |
|---|---|
| Camel milk | 20% |
| Stearic acid | 3.2% |
| Glycerin | 5% |
| Silicone | 0.5% |
| Triethanolamine | 1.2% |
| Vaseline | 5% |
| Polyethylene glycol | 5% |
| Nipagin | 0.1% |
| Nipasol | 0.1% |
| Vitamin e | 0.05% |
| Vitamin a | 100000 ui |
| Water to | 100% |

The cream regenerates and protects the skin.

Example 4

Shampoo was prepared by mixing:

| | |
|---|---|
| Fat fraction of camel milk | 3% |
| Sodium lauryl ethoxy sulfate | 40% |
| Coconut oil | 2% |
| Nipagin | 0.1% |
| Nipasol | 0.1% |
| Perfume natural | 0.1% |
| Water to | 100% |

Example 5

Conditioner was prepared by mixing:

| | |
|---|---|
| Fat fraction of camel milk | 3% |
| Cetyl alcohol | 4% |
| Glycerol | 5% |
| Cetyl trimethyl ammonium | 1% |
| Nipagin | 0.1% |
| Nipasol | 0.1% |
| Perfume natural | 0.1% |
| Water to | 100% |

Example 6

Solid soap was prepared by mixing:

| | |
|---|---|
| Fat fraction of camel milk | 3% |
| Palm oil | 15% |
| Coconut oil | 15% |
| Olive oil | 15% |
| Beeswax | 15% |
| Perfume natural | 0.1% |
| Water to | 100% |

Example 7

Liquid soap was prepared by mixing:

| | |
|---|---|
| Fat fraction of camel milk | 3% |
| Sodium lauryl sulfate | 40% |
| Sorbitol | 10% |
| Coconut oil | 2% |
| Nipagin | 0.1% |
| Nipasol | 0.1% |
| Perfume natural | 0.1% |
| Water to | 100% |

Example 8

Concentrated camel milk cream was prepared by mixing:

| | |
|---|---|
| Camel milk | 30% |
| Stearic alcohol | 25% |
| Propylene glycol | 12% |
| Sodium lauryl sulfate | 1% |
| Vaseline | 5% |
| Nipagin | 0.2% |
| Nipasol | 0.2% |
| Perfume natural | 0.1% |
| Water to | 100% |

Example 9

Body cream was prepared by mixing:

| | |
|---|---|
| Camel milk | 20% |
| Stearic acid | 5% |
| Cetyl alcohol | 1.8% |
| Vaseline | 10% |
| Polyethylene glycol (PEG) 400 | 5% |
| Glycerol | 5% |
| Triethanolamine | 1.2% |
| Nipagin | 0.1% |
| Nipasol | 0.1% |
| Silicone | 0.5% |
| Perfume natural | 0.1% |
| Water to | 100% |

Example 10

Cream of Example 9 was tried in Kibbutz Lahav in the Negev desert (Israel), on the sample of 119 participants, comprising the members of the Kibbutz and their friends. The cream was applied on various parts of the body, and at various occasions, as shown in the following table.

| Application | Number of participants |
|---|---|
| Hands | 119 |
| Face | 74 |
| Feet | 99 |
| Small wounds | 50 |
| Sun burns | 32 |
| Dry and chapped skin | 76 |

The participants were asked to assess various aspects of the cream quality by giving from one to four points, according to their satisfaction. The results are in the following table ("n.a." means no answer).

| | Degree of satisfaction | | | | |
|---|---|---|---|---|---|
| Aspect | 1 | 2 | 3 | 4 | n.a. |
| Texture of the cream | | 2 | 28 | 87 | 2 |
| Quick absorption into skin | | 1 | 78 | 38 | 2 |
| Skin softening | | 1 | 14 | 104 | |
| Skin moistening | | 1 | 25 | 92 | 1 |
| Small wounds healing | | | 29 | 51 | 39 |
| Sun burns healing | | | 4 | 28 | 87 |

The cream was applied once or twice a day. "N.a." means also that no wounds or burns were present.

The results show that the degree of satisfaction was quite high. No side effects were reported by any of the participants.

Example 11

Cream with camel milk was prepared by mixing:

| | |
|---|---|
| Camel milk | 20% |
| Stearic acid | 3.2% |
| Vaseline | 10% |
| Glycerol monostearate | 1.2% |
| Glycerol | 5% |
| Triethanolamine | 1.5% |
| Nipagin | 0.1% |
| Nipasol | 0.1% |

-continued

| | |
|---|---|
| Perfume natural | 0.1% |
| Water to | 100% |

Smooth, well moistening cream was obtained.

Example 12

| Foot cream | |
|---|---|
| Paraffin | 4 |
| Stearic acid | 3 |
| Glyceryl stearate | 4 |
| Cetyl alcohol | 4 |
| Shea butter | 2.5 |
| Silicone 350 | 0.5 |
| Lanoline | 2 |
| Isopropyl myristate | 4 |
| Almond oil | 1 |
| Jojoba oil | 1 |
| Zinc oxide | 0.25 |
| BHT | 0.04 |
| EDTA | 0.25 |
| Propylene glycol | 2.5 |
| *Aloe vera* spray dried power | 0.2 |
| Carbopol | 0.25 |
| Alantoine | 0.3 |
| Tocopheryl acetate | 0.5 |
| Retynil palmitate | 0.15 |
| PEG 400 | 5 |
| Camel milk | 40 |
| Starch | 0.8 |
| Perfume c.s. | |
| Dmdm-hydantoine | 0.6 |
| Phenonip | 1 |
| Calendula oil | 0.1 |
| Triethanolamine | 1.5 |
| Salicylic acid | 3 |
| Water to | 100 |

Example 13

| Hair conditioner | |
|---|---|
| Urea | 2 |
| Queratine | 0.5 |
| Pantenol | 0.5 |
| Ceramide | 0.4 |
| Cetyl alcohol | 4 |
| Glyceryl stearate | 0.8 |
| Isopropyl myristate | 1 |
| Lanoline | 0.5 |
| Dimeticone 100 | 0.5 |
| Polyvinylpyrrolidone k 30 | 1 |
| Nipagin | 0.1 |
| Nipasol | 0.1 |
| Cetyltrimethylammonium chloride | 5 |
| Camel milk | 20 |
| Water to | 100 |

Example 14

| Hand cream | |
|---|---|
| Stearic acid | 2.15 |
| Paraffin | 5 |
| Glyceryl stearate | 1.2 |
| Vaseline | 1.5 |
| Cetyl alcohol | 4 |
| Silicone 350 | 0.25 |
| Retinyl palmitate | 0.2 |
| Alpha tocopherol | 0.5 |
| Camel milk | 20 |
| Glycerin | 5 |
| Peg 400 | 5 |
| Imidazolidinyl urea | 0.6 |
| Phenoxyethanol | 0.7 |
| Triethanolamine | 1 |
| Nipagin | 0.4 |
| Nipasol | 0.4 |
| Carbomer | 0.2 |
| Lactic acid c.s. | |
| Perfume c.s. | |
| Tween 20 | 0.1 |
| Water to | 100 |

Example 15

| Hyaluronic acid emulsion | |
|---|---|
| Ceteareth 6 | 2 |
| Ceteareth 25 | 2 |
| Cetearyl octonate | 4 |
| Stearyl alcohol | 1.5 |
| Glyceryl stearate | 0.5 |
| Dimeticone 100 | 0.5 |
| Vaseline | 5 |
| Bisabolol | 0.3 |
| Camel milk | 20 |
| Carbomer | 0.4 |
| Pantenol | 0.5 |
| Propylene glycol | 3 |
| Methylparabene | 0.1 |
| Propyl parabene | 0.1 |
| Triethanolamine c.s. | |
| Perfume c.s. | |
| Sodium hyaluronate | 1 |
| Water to | 100 |

Example 16

| Hippopae cream | |
|---|---|
| Hippopae oil | 10 |
| Stearic acid | 1.75 |
| Cetyl alcohol | 1.5 |
| Glyceryl stearate | 2 |
| Paraffin | 7 |
| Jojoba oil | 1 |
| Almond oil | 1 |
| Lanoline | 1.5 |
| Shea butter | 1 |
| Triethanolamine | 0.8 |
| Camel milk | 40 |
| Glycerin | 3 |
| Propyleneglycol | 1 |

-continued

| Hippopae cream | |
|---|---|
| *Aloe vera* spray dried power | 0.2 |
| Phenonip | 1 |
| Imidazolidinyl urea | 0.6 |
| BHT | 0.04 |
| BHA | 0.04 |
| Water to | 100 |

Example 17

| Koubo cream | |
|---|---|
| Cereus peruvianus ext (Koubo) | 3 |
| Uninontan u-34 | 2 |
| Tri-k protective milk | 3 |
| *Allium cepa* ext | 3 |
| Allantoine | 3 |
| Lanol 14 | 2 |
| *Rosa centifolia* | 3 |
| Sepiwhite | 2 |
| Camel milk | 40 |
| Stearic acid | 3 |
| Triethanolamina | 1 |
| Paraffin | 5 |
| Vaseline | 1 |
| Lanoline | 1.5 |
| Phenonip | 0.6 |
| Imidazolidinyl urea | 0.6 |
| BHT | 0.02 |
| BHA | 0.02 |
| Water to | 100 |

Example 18

| Massage cream | |
|---|---|
| Polawax | 9 |
| Vaseline | 12 |
| Paraffin oil | 6 |
| Lanolin | 4 |
| Isopropyl myristate | 3 |
| Nipagin | 0.3 |
| Nipasol | 0.1 |
| Beeswax | 2 |
| Glycerin | 6 |
| Dmdm-hydantoin | 0.6 |
| Tocopherol hc | 0.5 |
| Camel milk | 20 |
| Water to | 100 |

Example 19

| Shampoo gel | |
|---|---|
| EDTA | 1 |
| Phenonip | 1 |
| Carbomer | 1 |
| Amisoft CS-12 | 25 |
| Jojoba oil | 3 |
| Camel milk lipids | 3 |

-continued

| Shampoo gel | |
|---|---|
| Glycerin | 5 |
| Amidobetaine C | 5 |
| Triethanolamine c.s. | |
| Cocoimidazoline dicarboxylate | 5 |
| Water | 100 |

Example 20

| Shaving cream | |
|---|---|
| Stearic acid | 14 |
| Shea butter | 2 |
| Lanoline | 3 |
| Paraffin | 3 |
| Jojoba oil | 2 |
| Camel milk | 20 |
| Carbomer | 1 |
| Alantoine | 2 |
| Triethanolamine | 2 |
| PEG 400 | 3.5 |
| Glycerin | 1.5 |
| Water to | 100 |

Example 21

| Soap | |
|---|---|
| Glycerin soap | 87 |
| Camel milk | 10 |
| Amidobetaine c | 2 |
| Perfume | 1 |

Example 22

| Special cream | |
|---|---|
| Paraffin | 7 |
| Stearine | 1.75 |
| Lanoline | 1.5 |
| Glyceryl stearate | 2.25 |
| Cetyl alcohol | 2.5 |
| Silicone 350 | 0.3 |
| Propyleneglycol | 1 |
| Glycerin | 3 |
| Camel milk | 20 |
| Carbomer | 0.25 |
| Triethanolamine | 0.8 |
| Phenonip | 1 |
| Perfume | 0.25 |
| BHT | 0.04 |
| Germal 115 | 0.6 |
| Lactic acid c.s. | |
| Parsol MCX | 2 |
| *Aloe vera* dried spray power | 0.2 |
| Shea butter | 1 |
| Water to | 100 |

Example 23

| Squalene and camel milk cream | |
|---|---|
| Carbomer | 3 |
| Propylene glycol | 6 |
| Phenonip | 1 |
| Polawax | 20 |
| PEG 400 | 1.5 |
| Glyceryl stearate | 0.5 |
| Silicone 350 | 1 |
| Paraffin | 5 |
| Squalene | 0.5 |
| Lanol 14 | 1.5 |
| Camel milk | 20 |
| Triethanolamine c.s | |
| Water | 100 |

Example 24

| Sun protector cream | |
|---|---|
| 2-Etylhexyl-p-metoxycinnamate | 4 |
| 2-Hydroxy-4-metoxybenzofenone | 3.5 |
| 2-Hydroxy-4-metoxybenzenesulfonic acid | 2.5 |
| Stearic acid | 5 |
| Cetyl alcohol | 10 |
| Titanium dioxide micronized | 2.5 |
| Glyceryl stearate | 5 |
| BHT | 0.004 |
| BHA | 0.004 |
| Metylparabene | 0.2 |
| Propylparabene | 0.1 |
| PVP/eicosane copolymer | 4 |
| Dimeticone 100 | 1 |
| Triethanolamine | 1.3 |
| Polysorbate 20 | 2 |
| Paraffin | 5 |
| Calendula oil | 2 |
| Camel milk | 20 |
| Water to | 100 |

Example 25

| Sun protector water resistant | |
|---|---|
| Camel milk | 20 |
| Pemulen tr II | 0.6 |
| Tween 80 | 0.2 |
| Glyceryl monostearate | 4 |
| Isopropyl myristate | 2 |
| Carbopol | 3 |
| Avalure 450 | 5 |
| Paraffin | 15 |
| Silicone 556 | 2 |
| Parsol mcx | 5 |
| Uvinul m40 | 6 |
| Neo heliopan | 2 |
| Parsol ocr | 2 |
| Triethanolamine c.s. | |
| Phenonip | 1 |
| Imidazolidinyl urea | 0.6 |
| Water to | 100 |

Example 26

| Veterinary cream | |
|---|---|
| Vaseline | 25 |
| Stearic alcohol | 25 |
| Propylene glycol | 12 |
| Sodium laurylsulfate | 1 |
| Metylparabene | 0.2 |
| Propylparabene | 0.2 |
| Camel milk | 20 |
| Aloe vera spray dried powder | 0.2 |
| Dmdm-hydantoine | 0.6 |
| Water to | 100 |

Example 27

| Cream 40% | |
|---|---|
| Paraffin | 7 |
| Stearic acid | 2.5 |
| Glyceryl stearate | 3 |
| Shea butter | 1 |
| Lanoline | 2.5 |
| Almonds oil | 1 |
| Silicone 350 | 0.2 |
| Carbomer | 0.2 |
| Propylene glycol | 5 |
| EDTA | 0.5 |
| Phenoxyethanol | 0.7 |
| Nipagin | 0.4 |
| Nipasol | 0.4 |
| Imidazolidinyl urea | 0.2 |
| Diazolidinyl urea | 0.2 |
| Dmdm-hydantoine | 0.2 |
| Triethanolamine | 1 |
| Perfume c.s. | |
| Lactic acid c.s. | |
| Camel milk | 40 |
| Aloe vera spray dried powder | 0.2 |
| Water to | 100 |

Example 28

| Face serum | |
|---|---|
| Lanol 1688 | 5 |
| Polawax gp-200 | 4 |
| PEG 400 | 4 |
| Nipagin | 0.1 |
| Nipasol | 0.1 |
| Phenonip | 0.8 |
| Dmdm-hydantoine | 0.3 |
| Hyaluronidate sodium | 1 |
| Tocopheryl acetate | 1 |
| Parsol mcx | 3 |
| Camel milk | 20 |
| Propylene glycol | 2 |
| Perfume c.s. | |
| Lactic acid c.s. | |
| Na-dl-2-pyrrolidone-5-carboxylate | 4 |
| Water to | 100 |

Example 29

Face night cream

| | |
|---|---|
| Paraffin | 5.7 |
| Lanoline | 1.5 |
| Stearic acid | 1.5 |
| Cetyl alcohol | 2.25 |
| Glyceryl stearate | 2 |
| Jojoba oil | 1 |
| Almonds oil | 2 |
| Isopropyl myristate | 1 |
| Silicone 350 | 0.3 |
| Carbomer | 0.35 |
| Triethanolamine | 0.8 |
| Phenoxyethanol | 0.7 |
| Imidazolidinyl urea | 0.6 |
| Perfume c.s. | |
| Glycerin | 4 |
| Camel milk | 20 |
| Nipagin | 0.4 |
| Nipasol | 0.4 |
| Water to | 100 |

Example 30

Face cream

| | |
|---|---|
| Paraffin | 7 |
| Stearic acid | 1.75 |
| Lanoline | 1.5 |
| Glyceryl stearate | 2.25 |
| Cetyl alcohol | 2.5 |
| Silicone 350 | 0.3 |
| Carbomer | 0.25 |
| Propylene glycol | 1 |
| Glycerin | 3 |
| Triethanolamine | 0.8 |
| Phenoxyethanol | 0.7 |
| Nipagin | 0.4 |
| Nipazol | 0.4 |
| Perfume | 0.25 |
| BHT | 0.04 |
| Imidazolidinyl urea | 0.6 |
| Lactic acid c.s. | |
| Camel milk | 20 |
| Water to | 100 |

Example 31

Cream antipruritus

| | |
|---|---|
| Paraffin | 7 |
| Stearic acid | 2.5 |
| Glyceryl stearate | 3 |
| Shea butter | 1 |
| Lanoline | 2.5 |
| Almonds oil | 1 |
| Silicone 350 | 0.2 |
| Carbomer | 0.2 |
| Propylene glycol | 5 |
| EDTA | 0.5 |
| Phenoxyethanol | 0.7 |
| Nipagin | 0.4 |
| Nipasol | 0.4 |
| Imidazolidinyl urea | 0.2 |
| Diazolidinyl urea | 0.2 |
| Dmdm-hydantoine | 0.2 |
| Triethanolamine | 1 |
| Perfume c.s. | |
| Lactic acid c.s. | |
| Camel milk | 40 |
| *Aloe vera* spray dried powder | 0.2 |
| Lemon oil | 5 |
| Water to | 100 |

Example 32

Cream antiaging

| | |
|---|---|
| Rose hip oil | 5 |
| Vitamin C | 3 |
| Vitamin E | 2 |
| Vitamin A | 0.5 |
| Peg 40 castor oil hydrogenated | 5 |
| Ceteareth | 4 |
| Ceteareth | 6 |
| Glyceryl stearate | 5 |
| Cetearyl octanate | 5 |
| Propylene glycol | 3 |
| Metyl parabene | 0.1 |
| Propyl parabene | 0.1 |
| BHT | 0.025 |
| BHA | 0.025 |
| Camel milk | 20 |
| Water to | 100 |

Example 33

Celulitis cream

| | |
|---|---|
| *Centella asiatic* | 2 |
| *Hedera helix* | 1 |
| Camphor | 1 |
| Menthol | 1 |
| Alcohol | 5 |
| Polywax | 5 |
| Paraffin | 10 |
| Isopropyl myristate | 5 |
| Vaseline | 5 |
| Silicone 350 | 1 |
| Glyceryl stearate | 10 |
| BHT | 0.04 |
| Metylparabene | 0.2 |
| Propylparabene | 0.2 |
| Polysorbate 20 | 1.8 |
| Camel milk | 20 |
| Triethanolamine | 0.5 |
| Water to | 100 |

Example 34

Camelia shower milk

| | |
|---|---|
| Sodium laurylsulfate | 13 |
| Amiisoft cs-12 | 2 |

-continued

| Camelia shower milk | |
|---|---|
| Nipagin | 0.2 |
| Dmdm-h | 0.3 |
| Glycerin | 5 |
| PEG 400 | 2 |
| Glycerol monostearate - se | 3 |
| Camel milk | 10 |
| Citric acid | 0.15 |
| Aminobetaine-c | 5 |
| Perfum | 0.7 |
| Lauramide | 3 |
| Water to | 100 |

Example 35

| Body cream | |
|---|---|
| Vaseline | 2 |
| Paraffin | 5 |
| Stearine | 2 |
| Cetyl alcohol | 3 |
| Silicone 350 | 0.350 |
| Almond oil | 1 |
| Carbomer | 0.28 |
| Triethanolamine | 1 |
| PEG 400 | 5 |
| Glycerin | 5 |
| Camel milk | 20 |
| Phenonip | 0.2 |
| Diazolidinyl urea | 0.25 |
| Perfume | 0.25 |
| Dmdm-h | 0.25 |
| Nipagin | 0.2 |
| Nipazol | 0.2 |
| Lactic acid c.s. | |
| Water to | 100 |

Example 36

| Antipsoriasis cream | |
|---|---|
| Stearic acid | 1.75 |
| Cetyl alcohol | 1.5 |
| Glyceryl stearate | 2 |
| Paraffin | 7 |
| Jojoba oil | 1 |
| Almonds oil | 1 |
| Lanoline | 1.5 |
| Shea butter | 1 |
| Triethanolamine | 0.8 |
| Camel milk | 40 |
| Glycerin | 3 |
| Propylene glycol | 1 |
| *Aloe vera* spray dried powder | 0.2 |
| Phenonip | 1 |
| Imidazolidinyl urea | 0.6 |
| BHT | 0.04 |
| BHA | 0.04 |
| Urea | 10 |
| Sulfur | 3 |
| Water to | 100 |

Example 37

| Antiacne cream | |
|---|---|
| Sepicontrol a5 | 4 |
| Caprylic capric tryglycerides | 5 |
| Phenonip | 1 |
| Imidazolidinyl urea | 0.6 |
| Sepigel 305 | 2.5 |
| Silicone 350 | 0.3 |
| Paraffin | 5 |
| Shea butter | 1 |
| Jojoba oil | 1 |
| Almonds oil | 1 |
| Camel milk | 20 |
| Lanoline | 1 |
| Allantoine | 1 |
| Water to | 100 |

Example 38

| Anti wrinkle cream | |
|---|---|
| Furfuryl adenine | 0.1 |
| Propylene glycol | 5 |
| Phenonip | 1 |
| Perfume c.s. | |
| Lactic acid c.s. | |
| Triethanolamine | 1 |
| Stearic acid | 2 |
| Paraffin | 7 |
| Glyceryl stearate | 3 |
| Shea butter | 1 |
| Lanoline | 2.5 |
| Almonds oil | 1 |
| Silicone 350 | 0.3 |
| Carbomer | 0.4 |
| EDTA | 0.05 |
| Imidazolidinyl urea | 0.6 |
| Camel milk | 20 |
| Water to | 100 |

Example 39

| After shave cream | |
|---|---|
| Natrosol | 0.5 |
| Glycerin | 3 |
| Isopropyl myristate | 10 |
| Silicone 350 | 1 |
| Alcohol | 10 |
| Imidazolidinyl urea | 0.3 |
| Nipagin | 0.4 |
| Nipasol | 0.4 |
| Perfume c.s. | |
| Camel milk lipids | 1.5 |
| Cetyl alcohol | 1 |
| Lactic acid c.s. | |
| Dipalmitoylethyl hydroxyethyl ammonium methosulfate | 2.2 |
| Water to | 100 |

Example 40

| Face serum | |
|---|---|
| Glycerin | 15 |
| Camel milk | 20 |
| Carbopol | 0.3 |
| PEG 400 | 4 |
| Nipagin | 0.2 |
| Alcohol | 2 |
| Dmdm-hydantoine | 0.2 |
| Parsol mcx | 0.2 |
| Benzofenone 4 | 0.2 |
| Tocopherol acetate | 2.5 |
| Ascorbic acid | 0.2 |
| Perfume c.s. | |
| Triethanolamine | 0.6 |
| Water to | 100 |

While this invention has been described in terms of some specific examples, many modifications and variations are possible. It is therefore understood that within the scope of the appended claims, the invention may be realized otherwise than as specifically described.

The invention claimed is:

1. A non-allergenic cosmetic composition containing mammalian milk, comprising heat-treated and stabilized camel milk and at least one extraneous lipid component selected from the group consisting of waxes, wherein said camel milk underwent heating at a temperature between about 65° C. and 72° C. for about 15 minutes.

2. A cosmetic composition according to claim 1, wherein said camel milk comprises a stabilizer selected from the group consisting of antioxidants, antiseptics, preservatives, surfactants, perfumes, vitamin A, vitamin E, vitamin C, and mixtures thereof.

3. A cosmetic composition according to claim 1, further comprising cosmetically-acceptable carriers.

4. A cosmetic composition according to claim 1, further comprising a polyalcohol.

5. A cosmetic composition according to claim 4, wherein said polyalcohol is selected from the group consisting of glycerol, propylene glycol, sorbitol, and polyethylene glycol.

6. A cosmetic composition according to claim 1, which is a homogeneous mixture in a form of liquid, cream, lotion, ointment, pomade, gel, or hard paste.

7. A cosmetic composition according to claim 1, which is a water-in-oil emulsion or oil-in-water emulsion.

8. A cosmetic composition according to claim 1, further comprising a component affecting its aspect, scent, or consistency.

9. A cosmetic composition according to claim 1, comprising camel milk in a concentration of from 3.0 to 40% w/w.

10. A cosmetic composition according to claim 1, wherein said lipid component has a concentration of from 3-65% w/w.

11. A cosmetic composition according to claim 4, wherein said polyalcohol component has a concentration of from 0 to 15% w/w.

12. A cosmetic product comprising a composition according to claim 1, which is a shaving cream, or shampoo, or soap, or conditioner, or body cream, or hand crème, or face cream, or body lotion.

13. A process for preparation of a cosmetic composition according to claim 1, comprising:
  i) providing camel milk;
  ii) heating said camel milk at a temperature between about 65° C. and 72° C. for about 15 minutes; and
  iii) mixing said camel milk with a lipid component, water, and at least another constituent selected from the group consisting of polyalcohol, surfactant, a component affecting aspect, scent or consistency, antioxidant, stabilizer, vitamin A, vitamin E, and antiseptic materials, wherein said components are mixed in any order until homogeneity is achieved.

14. A process according to claim 13, further comprising adding to said camel milk or to said camel milk after said heating a stabilizer selected from the group consisting of antioxidants, antiseptics, and preservatives.

15. A process according to claim 13, further comprising at least one method selected from the group consisting of evaporation, lyophylization, precipitation, filtration, extraction, heat treatment, centrifugation, chromatography, enzymatic treatment, and microbial treatment.

16. A process according to claim 13, comprising a further heat treatment.

* * * * *